United States Patent
Levin et al.

(10) Patent No.: US 6,906,232 B2
(45) Date of Patent: *Jun. 14, 2005

(54) MOLECULAR SIEVE COMPOSITIONS, CATALYSTS THEREOF, THEIR MAKING AND USE IN CONVERSION PROCESSES

(75) Inventors: Doron Levin, Annadale, NJ (US); James Clark Vartuli, Schwenksville, PA (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 138 days.

This patent is subject to a terminal disclaimer.

(21) Appl. No.: 10/215,511

(22) Filed: Aug. 9, 2002

(65) Prior Publication Data

US 2004/0030213 A1 Feb. 12, 2004

(51) Int. Cl.$^7$ ................................................. C07C 1/20
(52) U.S. Cl. ...................... 585/638; 585/639; 585/640; 585/641; 585/642
(58) Field of Search ............................... 585/638, 639, 585/640, 641, 642

(56) References Cited

U.S. PATENT DOCUMENTS

| | | | |
|---|---|---|---|
| 4,377,294 A | 3/1983 | Lockwood et al. | ... 280/154.5 R |
| 4,465,889 A | 8/1984 | Anthony et al. | ............ 585/640 |
| 4,471,150 A | 9/1984 | Wu | ............. 585/640 |
| 4,481,376 A | 11/1984 | Wunder et al. | ............. 585/640 |
| 4,663,305 A | 5/1987 | Mauldin et al. | ............. 502/304 |
| 4,664,780 A | 5/1987 | Lochow et al. | ............. 208/120 |
| 4,769,509 A | 9/1988 | Josefowicz | ................. 585/500 |
| 5,047,379 A | 9/1991 | Alyea et al. | .................. 502/79 |
| 5,130,114 A | 7/1992 | Igarashi | ...................... 423/652 |
| 5,208,200 A | 5/1993 | Soled et al. | ................. 502/241 |
| 5,227,352 A | 7/1993 | Tsujii et al. | .................. 502/65 |
| 5,347,056 A | 9/1994 | Watanabe et al. | ........... 568/881 |
| 5,371,312 A * | 12/1994 | Lago et al. | ................. 585/475 |
| 5,417,949 A | 5/1995 | McWilliams et al. | .... 423/239.2 |
| 5,430,000 A | 7/1995 | Timken | ........................ 502/60 |
| 5,728,644 A | 3/1998 | Ho et al. | ..................... 502/322 |
| 5,977,425 A | 11/1999 | Brandes et al. | ............. 585/734 |
| 6,046,373 A | 4/2000 | Sun | ............................. 585/640 |
| 6,114,268 A | 9/2000 | Wu et al. | ...................... 502/74 |
| 6,180,828 B1 | 1/2001 | Hidaka et al. | .............. 564/479 |
| 6,228,799 B1 | 5/2001 | Aubert et al. | ................ 502/304 |
| 2001/0002383 A1 | 5/2001 | Hidaka et al. | ................. 502/72 |
| 2002/0013505 A1 | 1/2002 | Fung et al. | .................. 585/640 |
| 2004/0034178 A1 * | 2/2004 | Vaughn et al. | ................. 526/90 |

FOREIGN PATENT DOCUMENTS

| | | | |
|---|---|---|---|
| EP | 0 208 868 | 2/1990 | .......... C10G/11/02 |
| EP | 0 256 875 | 5/1996 | .......... C10G/11/05 |
| EP | 0 697 247 | 9/1999 | ........... B01J/29/06 |
| EP | 0 967 011 | 12/1999 | ........... B01J/29/06 |
| EP | 0 993 867 | 4/2000 | ........... B01J/29/85 |
| EP | 0 906 244 | 1/2002 | ........... C01J/25/00 |
| FR | 2 661 171 | 4/1990 | ........... C01G/25/02 |
| JP | 200138216 | 8/1999 | ........... B01J/33/00 |
| WO | WO 96/16142 | 5/1996 | .......... C01G/45/64 |
| WO | WO 98 29370 | 7/1998 | |
| WO | WO 99/41334 | 8/1999 | ........... C10G/71/00 |
| WO | WO 01/47810 | 7/2001 | ........... C01B/37/08 |
| WO | WO 01 64340 | 9/2001 | |
| WO | WO 02/05952 | 1/2002 | ............ B01J/29/84 |

OTHER PUBLICATIONS

Kang and Inui, *Effects of decrease in number of acid sites located on the external surface of Ni–SAPO–34 crystalline catalyst by the mechanochemical method*, Catalysis Letters 53, pp. 171–176 (1998).

* cited by examiner

*Primary Examiner*—Elizabeth D. Wood

(57) ABSTRACT

The invention relates to a conversion process of a feedstock, preferably an oxygenated feedstock, into one or more olefin(s), preferably ethylene and/or propylene, in the presence of a molecular sieve catalyst composition that includes a molecular sieve and a Group 3 metal oxide and/or an oxide of a Lanthanide or Actinide series element. The invention is also directed to methods of making and formulating the molecular sieve catalyst composition useful in a conversion process of a feedstock into one or more olefin(s).

24 Claims, No Drawings

MOLECULAR SIEVE COMPOSITIONS, CATALYSTS THEREOF, THEIR MAKING AND USE IN CONVERSION PROCESSES

FIELD OF THE INVENTION

The present invention relates to a conversion process utilizing a molecular sieve composition or a molecular sieve catalyst composition to form olefin(s). The invention is also directed to a method of making the molecular sieve composition and the molecular sieve catalyst composition.

BACKGROUND OF THE INVENTION

Olefins are traditionally produced from petroleum feedstock by catalytic or steam cracking processes. These cracking processes, especially steam cracking, produce light olefin(s) such as ethylene and/or propylene from a variety of hydrocarbon feedstock. Ethylene and propylene are important commodity petrochemicals useful in a variety of processes for making plastics and other chemical compounds.

The petrochemical industry has known for some time that oxygenates, especially alcohols, are convertible into light olefin(s). There are numerous technologies available for producing oxygenates including fermentation or reaction of synthesis gas derived from natural gas, petroleum liquids, carbonaceous materials including coal, recycled plastics, municipal waste or any other organic material. Generally, the production of synthesis gas involves a combustion reaction of natural gas, mostly methane, and an oxygen source into hydrogen, carbon monoxide and/or carbon dioxide. Syngas production processes are well known, and include conventional steam reforming, autothermal reforming, or a combination thereof.

Methanol, the preferred alcohol for light olefin production, is typically synthesized from the catalytic reaction of hydrogen, carbon monoxide and/or carbon dioxide in a methanol reactor in the presence of a heterogeneous catalyst. For example, in one synthesis process methanol is produced using a copper/zinc oxide catalyst in a water-cooled tubular methanol reactor. The preferred conversion process converts a feedstock containing methanol in the presence of a molecular sieve catalyst composition to form one or more olefin(s), primarily ethylene and/or propylene.

Molecular sieves are porous solids having pores of different sizes such as zeolites or zeolite-type molecular sieves, carbons and oxides. The most commercially useful molecular sieves for the petroleum and petrochemical industries are known as zeolites, for example aluminosilicate molecular sieves. Zeolites in general have a one-, two- or three-dimensional crystalline pore structure having uniformly sized pores of molecular dimensions that selectively adsorb molecules that can enter the pores, and exclude those molecules that are too large.

There are many different types of molecular sieves well known to convert a feedstock, especially an oxygenate containing feedstock, into one or more olefin(s). For example, U.S. Pat. No. 5,367,100 describes the use of a well known zeolite, ZSM-5, to convert methanol into olefin(s); U.S. Pat. No. 4,062,905 discusses the conversion of methanol and other oxygenates to ethylene and propylene using crystalline aluminosilicate zeolites, for example Zeolite T, ZK5, erionite and chabazite; U.S. Pat. No. 4,079,095 describes the use of ZSM-34 to convert methanol to hydrocarbon products such as ethylene and propylene; and U.S. Pat. No. 4,310,440 describes producing light olefin(s) from an alcohol using a crystalline aluminophosphates, often represented by $AlPO_4$.

One of the most useful molecular sieves for converting methanol to olefin(s) is a silicoaluminophosphate molecular sieves. Silicoaluminophosphate (SAPO) molecular sieves contain a three-dimensional microporous crystalline framework structure of $[SiO_2]$, $[AlO_2]$ and $[PO_2]$ corner sharing tetrahedral units. SAPO synthesis is described in U.S. Pat. No. 4,440,871, which is herein fully incorporated by reference. SAPO is generally synthesized by the hydrothermal crystallization of a reaction mixture of silicon-, aluminum- and phosphorus-sources and at least one templating agent. Synthesis of a SAPO molecular sieve, its formulation into a SAPO catalyst, and its use in converting a hydrocarbon feedstock into olefin(s), particularly where the feedstock is methanol, is shown in U.S. Pat. Nos. 4,499,327, 4,677,242, 4,677,243, 4,873,390, 5,095,163, 5,714,662 and 6,166,282, all of which are herein fully incorporated by reference.

Typically, molecular sieves are formed into molecular sieve catalyst compositions to improve their durability in commercial conversion processes. These molecular sieve catalyst compositions are formed by combining a molecular sieve and a matrix material usually in the presence of a binder. The purpose of the binder is hold the matrix material, often a clay, to the molecular sieve. Binders and matrix materials are typically metal oxides that have a very small surface area such as less than ten square meters per gram ($m^2/g$), more likely less than one $m^2/g$ of metal oxide. The use of binders and matrix materials in the formation of molecular sieve catalyst compositions is well known.

U.S. Pat. No. 4,465,889 describes a catalyst composition of a silicalite molecular sieve impregnated with a thorium, zirconium, or a titanium metal oxide for use in converting methanol, dimethyl ether, or a mixture thereof into a hydrocarbon product rich in iso-$C_4$ compounds.

U.S. Pat. No. 6,180,828 discusses the use of a modified molecular sieve to produce methylamines from methanol and ammonia, where for example, a silicoaluminophosphate molecular sieve is combined with one of the modifiers, a zirconium oxide, a titanium oxide, a yttrium oxide, montmorillonite or kaolinite.

U.S. Pat. No. 5,417,949 relates to a process of converting noxious nitrogen oxides in an oxygen containing effluent into nitrogen and water using a molecular sieve and a metal oxide binder, where the preferred binder is titania and the molecular sieve is an aluminosilicate molecular sieve.

Although the use of binders and matrix materials are known for use with molecular sieves to form molecular sieve catalyst compositions, and that these catalyst compositions are useful in a process for converting oxygenates into olefin(s), these binders and matrix materials typically only serve to provide desired physical characteristics to the catalyst composition, and have little to no effect on conversion and selectivity of the molecular sieve. It would therefore be desirable to have an improved molecular sieve catalyst composition having better conversion rates, olefin selectivity, longer lifetimes, and commercially desirable operability and cost advantages.

SUMMARY OF THE INVENTION

This invention provides for a molecular sieve catalyst composition, a method for making or formulating the molecular sieve catalyst composition, and to their use in a conversion process for making one or more olefin(s), particularly light olefin(s).

In one embodiment the invention is directed to a method for making the molecular sieve composition of the invention by combining, contacting, mixing, or the like, a molecular sieve and an active Group 3 metal oxide or an active oxide of the Lanthanide or Actinide series of elements. The preferred metal of the Group 3 metal oxide of the invention are lanthanum, yttrium and scandium. The most preferred active metal oxides are scandium oxide, lanthanum oxide and yttrium oxide. More preferably the molecular sieve is synthesized from the combination of two or more of a silicon source, an aluminum source, and a phosphorous source, optionally in the presence of a templating agent.

In another embodiment the invention relates to a method for making a molecular sieve catalyst composition by combining, contacting, mixing, or the like, a matrix material, a binder, and at least one Group 3 metal oxide or at least one oxide of the Lanthanide or Actinide series elements, wherein the active metal oxide is different from the binder and/or the matrix material. Preferably the Group 3 metal oxide is a lanthanum metal oxide, a yttrium metal oxide or a scandium metal oxide, and the molecular sieve is synthesized from the combination of two or more of a silicon source, an aluminum source, and a phosphorous source, optionally in the presence of a templating agent. In a more preferred embodiment, the molecular sieve, the binder and the matrix material are made into a formulated molecular sieve catalyst composition that is then contacted, mixed, combined, spray dried, or the like, with a Group 3 metal oxide or an oxide of the Lanthanide or Actinide series elements. In an alternative embodiment, the Group 3 metal oxide or the oxide of the Lanthanide or Actinide series elements is included in the spray drying of the formulated molecular sieve catalyst composition.

In yet another preferred method of the invention, a molecular sieve catalyst composition is made by a method comprising the steps of: (i) synthesizing a molecular sieve by the method comprising the steps of: (a) forming a first reaction mixture of at least one templating agent and at least two of the group consisting of a silicon source, a phosphorous source and an aluminum source; and (b) removing the molecular sieve from the first reaction mixture; (ii) forming a Group 3 metal oxide and/or an oxide of the Lanthanide or Actinide series elements by the method comprising the steps of: (a) forming a second reaction mixture comprising a Group 3 metal oxide precursor and/or an oxide precursor of the Lanthanide or Actinide series elements and a precipitating agent, (b) removing the Group 3 metal oxide and/or the oxide of the Lanthanide or Actinide series elements from the second reaction mixture; and (iii) combining the molecular sieve and the active Group 3 metal oxide and/or the active oxide of the Lanthanide or Actinide series elements.

In yet another embodiment, the invention is directed to a process for producing olefin(s) in the presence of any of the above molecular sieve compositions and/or molecular sieve or formulated molecular sieve catalyst compositions. In particular, the process involves producing olefin(s) in a process for converting a feedstock, preferably a feedstock comprising an oxygenate, more preferably a feedstock comprising an alcohol, and most preferably a feedstock comprising methanol, in the presence of one or more of the molecular sieve compositions, or catalyst compositions discussed above.

The invention is also directed to a composition of matter of any one of the molecular sieve compositions and/or molecular sieve catalyst compositions described above. The invention is further directed to the use of a Group 3 metal oxide and/or an oxide of the Lanthanide or Actinide series elements in combination with a formulated molecular sieve catalyst composition comprising a matrix material and/or a binder, a molecular sieve, and where the Group 3 metal oxide and/or the oxide of the Lanthanide or Actinide series elements is different from the matrix material and/or the binder, for use in converting an oxygenated feedstock into one or more olefin(s).

DETAILED DESCRIPTION OF THE INVENTION

Introduction

The invention is directed toward a molecular sieve composition, to a catalyst composition thereof, and to their use in the conversion of hydrocarbon feedstocks, particularly oxygenated feedstocks, into olefin(s). It has been found that combining a molecular sieve with a Group 3 metal oxide and/or an oxide of the Lanthanide or Actinide series elements results in a molecular sieve composition or molecular sieve catalyst composition capable of converting more hydrocarbons, preferably oxygenates, more particularly methanol, preferably into one or more olefin(s) per gram of composition. The preferred metal oxides are those having a Group 3 metal (for example yttrium, scandium and lanthanum) and the Lanthanide or Actinide series elements (for example, cerium, neodymium, praseodymium and thorium) from the Periodic Table of Elements using the IUPAC format described in the *CRC Handbook of Chemistry and Physics*, 78th Edition, CRC Press, Boca Raton, Fla. (1997). Also, surprisingly, the molecular sieve compositions and catalyst compositions thereof have longer lifetimes because they are less susceptible to coke formation, which is well known to reduce conversion of hydrocarbons, preferably oxygenates, into olefin(s). It has also been discovered that the molecular sieve compositions and catalyst compositions thereof are more selective to olefin(s) such as propylene. In this regard, in particular in the conversion of an oxygenate to at least ethylene and propylene, the amount of unwanted ethane and propane made is reduced along with other problematic compounds such as aldehydes and ketones, specifically acetaldehyde. Lastly, without being bound to any particular theory, it is believed that because the molecular sieve composition and catalyst compositions thereof are of a higher density, they tend not to exit a typical conversion process reactor via the exiting effluent stream or from the top of a regenerator often utilized to remove coke from a catalyst composition. The higher density compositions are believed to improve operability in the overall process and lower, for example, catalyst composition losses thereby lowering overall conversion costs.

Molecular Sieves

Molecular sieves have various chemical, physical, and framework characteristics. Molecular sieves have been well classified by the Structure Commission of the International Zeolite Association according to the rules of the IUPAC Commission on Zeolite Nomenclature. A framework-type describes the topology and connectivity of the tetrahedrally coordinated atoms constituting the framework, and makes an abstraction of the specific properties for those materials. Framework-type zeolite and zeolite-type molecular sieves for which a structure has been established, are assigned a three letter code and are described in the *Atlas of Zeolite Framework Types*, 5th edition, Elsevier, London, England (2001), which is herein fully incorporated by reference.

Non-limiting examples of these molecular sieves are the small pore molecular sieves, AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted forms thereof; the medium pore molecular sieves, AFO, AEL, EUO, HEU, FER, MEL, MFI, MTW, MTT, TON, and substituted forms thereof; and the large pore molecular sieves, EMT, FAU, and substituted forms thereof. Other molecular sieves include ANA, BEA, CFI, CLO, DON, GIS, LTL, MER, MOR, MWW and SOD. Non-limiting examples of the preferred molecular sieves, particularly for converting an oxygenate containing feedstock into olefin(s), include AEL, AFY, BEA, CHA, EDI, FAU, FER, GIS, LTA, LTL, MER, MFI, MOR, MTT, MWW, TAM and TON. In one preferred embodiment, the molecular sieve of the invention has an AEI topology or a CHA topology, or a combination thereof, most preferably a CHA topology.

Crystalline molecular sieve materials all have 3-dimensional, four-connected framework structure of corner-sharing $TO_4$ tetrahedra, where T is any tetrahedrally coordinated cation. These molecular sieves are typically described in terms of the size of the ring that defines a pore, where the size is based on the number of T atoms in the ring. Other framework-type characteristics include the arrangement of rings that form a cage, and when present, the dimension of channels, and the spaces between the cages. See van Bekkum, et al., *Introduction to Zeolite Science and Practice, Second Completely Revised and Expanded Edition*, Volume 137, pages 1–67, Elsevier Science, B.V., Amsterdam, Netherlands (2001).

The small, medium and large pore molecular sieves have from a 4-ring to a 12-ring or greater framework-type. In a preferred embodiment, the zeolitic molecular sieves have 8-, 10- or 12-ring structures or larger and an average pore size in the range of from about 3 Å to 15 Å. In the most preferred embodiment, the molecular sieves, preferably silicoaluminophosphate molecular sieves, have 8-rings and an average pore size less than about 5 Å, preferably in the range of from 3 Å to about 5 Å, more preferably from 3 Å to about 4.5 Å, and most preferably from 3.5 Å to about 4.2 Å.

Molecular sieves have a molecular framework of one, preferably two or more corner-sharing $[TO_4]$ tetrahedral units, more preferably, two or more $[SiO_4]$, $[AlO_4]$ and/or $[PO_4]$ tetrahedral units, and most preferably $[SiO_4]$, $[AlO_4]$ and $[PO_4]$ tetrahedral units. These silicon, aluminum, and phosphorous based molecular sieves and metal containing silicon, aluminum and phosphorous based molecular sieves have been described in detail in numerous publications including for example, U.S. Pat. No. 4,567,029 (MeAPO where Me is Mg, Mn, Zn, or Co), U.S. Pat. No. 4,440,871 (SAPO), European Patent Application EP-A-0 159 624 (ELAPSO where El is As, Be, B, Cr, Co, Ga, Ge, Fe, Li, Mg, Mn, Ti or Zn), U.S. Pat. No. 4,554,143 (FeAPO), U.S. Pat. Nos. 4,822,478, 4,683,217, 4,744,885 (FeAPSO), EP-A-0 158 975 and U.S. Pat. No. 4,935,216 (ZnAPSO, EP-A-0 161 489 (CoAPSO), EP-A-0 158 976 (ELAPO, where EL is Co, Fe, Mg, Mn, Ti or Zn), U.S. Pat. No. 4,310,440 ($AlPO_4$), EP-A-0 158 350 (SENAPSO), U.S. Pat. No. 4,973,460 (LiAPSO), U.S. Pat. No. 4,789,535 (LiAPO), U.S. Pat. No. 4,992,250 (GeAPSO), U.S. Pat. No. 4,888,167 (GeAPO), U.S. Pat. No. 5,057,295 (BAPSO), U.S. Pat. No. 4,738,837 (CrAPSO), U.S. Pat. Nos. 4,759,919, and 4,851,106 (CrAPO), U.S. Pat. Nos. 4,758,419, 4,882,038, 5,434,326 and 5,478,787 (MgAPSO), U.S. Pat. No. 4,554,143 (FeAPO), U.S. Pat. No. 4,894,213 (AsAPSO), U.S. Pat. No. 4,913,888 (AsAPO), U.S. Pat. Nos. 4,686,092, 4,846,956 and 4,793,833 (MnAPSO), U.S. Pat. Nos. 5,345,011 and 6,156,931 (MnAPO), U.S. Pat. No. 4,737,353 (BeAPSO), U.S. Pat. No. 4,940,570 (BeAPO), U.S. Pat. Nos. 4,801,309, 4,684,617 and 4,880,520 (TiAPSO), U.S. Pat. Nos. 4,500, 651, 4,551,236 and 4,605,492 (TiAPO), U.S. Pat. Nos. 4,824,554, 4,744,970 (CoAPSO), U.S. Pat. No. 4,735,806 (GaAPSO) EP-A-0 293 937 (QAPSO, where Q is framework oxide unit $[QO_2]$), as well as U.S. Pat. Nos. 4,567,029, 4,686,093, 4,781,814, 4,793,984, 4,801,364, 4,853,197, 4,917,876, 4,952,384, 4,956,164, 4,956,165, 4,973,785, 5,241,093, 5,493,066 and 5,675,050, all of which are herein fully incorporated by reference.

Other molecular sieves include those described in R. Szostak, *Handbook of Molecular Sieves*, Van Nostrand Reinhold, New York, N.Y. (1992), which is herein fully incorporated by reference.

The more preferred silicon, aluminum and/or phosphorous containing molecular sieves, and aluminum, phosphorous, and optionally silicon, containing molecular sieves include aluminophosphate (AlPO) molecular sieves and silicoaluminophosphate (SAPO) molecular sieves and substituted, preferably metal substituted, AlPO and SAPO molecular sieves. The most preferred molecular sieves are SAPO molecular sieves, and metal substituted SAPO molecular sieves.

In one embodiment, the molecular sieve, as described in many of the U.S. patents mentioned above, is represented by the empirical formula, on an anhydrous basis:

$$mR:(M_xAl_yP_z)O_2$$

wherein R represents at least one templating agent, preferably an organic templating agent; m is the number of moles of R per mole of $(M_xAl_yP_z)O_2$ and m has a value from 0 to 1, preferably 0 to 0.5, and most preferably from 0 to 0.3; x, y, and z represent the mole fraction of Al, P and M as tetrahedral oxides, where M is a metal selected from one of Group IA, IIA, IB, IIIB, IVB, VB, VIIB, VIIB, VIIIB and Lanthanide's of the Periodic Table of Elements, preferably M is selected from one of the group consisting of Co, Cr, Cu, Fe, Ga, Ge, Mg, Mn, Ni, Sn, Ti, Zn and Zr. In an embodiment, m is greater than or equal to 0.2, and x, y and z are greater than or equal to 0.01. In another embodiment, m is greater than 0.1 to about 1, x is greater than 0 to about 0.25, y is in the range of from 0.4 to 0.5, and z is in the range of from 0.25 to 0.5, more preferably m is from 0.15 to 0.7, x is from 0.01 to 0.2, y is from 0.4 to 0.5, and z is from 0.3 to 0.5.

Non-limiting examples of SAPO and AlPO molecular sieves of the invention include one or a combination of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44 (U.S. Pat. No. 6,162,415), SAPO-47, SAPO-56, AlPO-5, AlPO-11, AlPO-18, AlPO-31, AlPO-34, AlPO-36, AlPO-37, AlPO-46, and metal containing molecular sieves thereof. The more preferred zeolite-type molecular sieves include one or a combination of SAPO-18, SAPO-34, SAPO-35, SAPO-44, SAPO-56, AlPO-18 and AlPO-34, even more preferably one or a combination of SAPO-18, SAPO-34, AlPO-34 and AlPO-18, and metal containing molecular sieves thereof, and most preferably one or a combination of SAPO-34 and AlPO-18, and metal containing molecular sieves thereof.

In an embodiment, the molecular sieve is an intergrowth material having two or more distinct phases of crystalline structures within one molecular sieve composition. In particular, intergrowth molecular sieves are described in the U.S. patent application Ser. No. 09/924,016 filed Aug. 7, 2001 and PCT WO 98/15496 published Apr. 16, 1998, both of which are herein fully incorporated by reference. For example, SAPO-18, AlPO-18 and RUW-18 have an AEI framework-type, and SAPO-34 has a CHA framework-type. In another embodiment, the molecular sieve comprises at least one intergrown phase of AEI and CHA framework-types, preferably the molecular sieve has a greater amount of CHA framework-type to AEI framework-type, and more preferably the ratio of CHA to AEI is greater than 1:1 as determined by the DIFFaX method disclosed in U.S. patent application Ser. No. 09/924,106 filed Aug. 7, 2001, which is fully incorporated herein by reference.

Molecular Sieve Synthesis

The synthesis of molecular sieves is described in many of the references discussed above. Generally, molecular sieves are synthesized by the hydrothermal crystallization of one or more of a source of aluminum, a source of phosphorous, a source of silicon, a templating agent, and a metal containing compound. Typically, a combination of sources of silicon, aluminum and phosphorous, optionally with one or more templating agents and/or one or more metal containing compounds are placed in a sealed pressure vessel, optionally lined with an inert plastic such as polytetrafluoroethylene, and heated, under a crystallization pressure and temperature, until a crystalline material is formed, and then recovered by filtration, centrifugation and/or decanting.

In a preferred embodiment the molecular sieves are synthesized by forming a reaction product of a source of silicon, a source of aluminum, a source of phosphorous, one or more organic templating agent, preferably nitrogen containing organic templating agent(s), and one or more active metal oxides. This particularly preferred embodiment results in the synthesis of a SAPO crystalline material that is then isolated by filtration, centrifugation and/or decanting.

Non-limiting examples of silicon sources include a silicates, fumed silica, for example, Aerosil-200 available from Degussa Inc., New York, N.Y., and CAB-O-SIL M-5, silicon compounds such as tetraalkyl orthosilicates, for example, tetramethyl orthosilicate (TMOS) and tetraethylorthosilicate (TEOS), colloidal silicas or aqueous suspensions thereof, for example Ludox-HS-40 sol available from E. I. du Pont de Nemours, Wilmington, Del., silicic acid, alkali-metal silicate, or any combination thereof. The preferred source of silicon is a silica sol.

Non-limiting examples of aluminum sources include aluminum-containing compositions such as aluminum alkoxides, for example aluminum isopropoxide, aluminum phosphate, aluminum hydroxide, sodium aluminate, pseudo-boehmite, gibbsite and aluminum trichloride, or any combinations thereof. A preferred source of aluminum is pseudo-boehmite, particularly when producing a silicoaluminophosphate molecular sieve.

Non-limiting examples of phosphorous sources, which may also include aluminum-containing phosphorous compositions, include phosphorous-containing, inorganic or organic, compositions such as phosphoric acid, organic phosphates such as triethyl phosphate, and crystalline or amorphous aluminophosphates such as $AlPO_4$, phosphorous salts, or combinations thereof. The preferred source of phosphorous is phosphoric acid, particularly when producing a silicoaluminophosphate.

Templating agents are generally compounds that contain elements of Group 15 of the Periodic Table of Elements, particularly nitrogen, phosphorus, arsenic and antimony, more preferably nitrogen or phosphorous, and most preferably nitrogen. Typical templating agents of Group 15 of the Periodic Table of elements also contain at least one alkyl or aryl group, preferably an alkyl or aryl group having from 1 to 10 carbon atoms, and more preferably from 1 to 8 carbon atoms. The preferred templating agents are nitrogen-containing compounds such as amines and quaternary ammonium compounds.

The quaternary ammonium compounds, in one embodiment, are represented by the general formula $R_4N^+$, where each R is hydrogen or a hydrocarbyl or substituted hydrocarbyl group, preferably an alkyl group or an aryl group having from 1 to 10 carbon atoms. In one embodiment, the templating agents include a combination of one or more quaternary ammonium compound(s) and one or more of a mono-, di- or tri-amine.

Non-limiting examples of templating agents include tetraalkyl ammonium compounds including salts thereof such as tetramethyl ammonium compounds including salts thereof, tetraethyl ammonium compounds including salts thereof, tetrapropyl ammonium compounds including salts thereof, and tetrabutylammonium compounds including salts thereof, cyclohexylamine, morpholine, di-n-propylamine (DPA), tripropylamine, triethylamine (TEA), triethanolamine, piperidine, cyclohexylamine, 2-methylpyridine, N,N-dimethylbenzylamine, N,N-diethylethanolamine, dicyclohexylamine, N,N-dimethylethanolamine, choline, N,N'-dimethylpiperazine, 1,4-diazabicyclo(2,2,2)octane, N',N',N,N-tetramethyl-(1,6) hexanediamine, N-methyldiethanolamine, N-methyl-ethanolamine, N-methyl piperidine, 3-methyl-piperidine, N-methylcyclohexylamine, 3-methylpyridine, 4-methylpyridine, quinuclidine, N,N'-dimethyl-1,4-diazabicyclo(2,2,2) octane ion; di-n-butylamine, neopentylamine, di-n-pentylamine, isopropylamine, t-butyl-amine, ethylenediamine, pyrrolidine, and 2-imidazolidone.

The preferred templating agent or template is a tetraethylammonium compound, such as tetraethyl ammonium hydroxide (TEAOH), tetraethyl ammonium phosphate, tetraethyl ammonium fluoride, tetraethyl ammonium bromide, tetraethyl ammonium chloride and tetraethyl ammonium acetate. The most preferred templating agent is TEAOH and salts thereof, particularly when producing a silicoaluminophosphate molecular sieve. In one embodiment, a combination of two or more of any of the above templating agents is used in combination with two or more of a silicon-, aluminum-, and phosphorous-source.

Generally, the synthesis mixture described above is sealed in a vessel and heated, preferably under autogenous pressure, to a temperature in the range of from about 80° C. to about 250° C., preferably from about 100° C. to about 250° C., more preferably from about 125° C. to about 225° C., even more preferably from about 150° C. to about 180° C.

In yet another embodiment, the crystallization temperature is increased gradually or stepwise during synthesis, preferably the crystallization temperature is maintained constant, for a period of time effective to form a crystalline product. The time required to form the crystalline product is typically from immediately up to several weeks, the duration of which is usually dependent on the temperature; the higher the temperature the shorter the duration. In one embodiment, the crystalline product is formed under heating from about 30 minutes to around 2 weeks, preferably from about 45 minutes to about 240 hours, and more preferably from about 1 hour to about 120 hours.

In one embodiment, the synthesis of a molecular sieve is aided by seeds from another or the same framework type molecular sieve.

The hydrothermal crystallization is carried out with or without agitation or stirring, for example stirring or tumbling. The stirring or agitation during the crystallization period may be continuous or intermittent, preferably continuous agitation. Typically, the crystalline molecular sieve product is formed, usually in a slurry state, and is recovered by any standard technique well known in the art, for example centrifugation or filtration. The isolated or separated crystalline product, in an embodiment, is washed, typically, using a liquid such as water, from one to many times. The washed crystalline product is then optionally dried, preferably in air.

One method for crystallization involves subjecting an aqueous reaction mixture containing an excess amount of a templating agent, subjecting the mixture to crystallization under hydrothermal conditions, establishing an equilibrium between molecular sieve formation and dissolution, and then, removing some of the excess templating agent and/or organic base to inhibit dissolution of the molecular sieve. See for example U.S. Pat. No. 5,296,208, which is herein fully incorporated by reference.

Other methods for synthesizing molecular sieves or modifying molecular sieves are described in U.S. Pat. No. 5,879,655 (controlling the ratio of the templating agent to phosphorous), U.S. Pat. No. 6,005,155 (use of a modifier without a salt), U.S. Pat. No. 5,475,182 (acid extraction), U.S. Pat. No. 5,962,762 (treatment with transition metal), U.S. Pat. Nos. 5,925,586 and 6,153,552 (phosphorous modified), U.S. Pat. No. 5,925,800 (monolith supported), U.S. Pat. No. 5,932,512 (fluorine treated), U.S. Pat. No. 6,046,373 (electromagnetic wave treated or modified), U.S. Pat. No. 6,051,746 (polynuclear aromatic modifier), U.S. Pat. No. 6,225,254 (heating template), PCT WO 01/36329 published May 25, 2001 (surfactant synthesis), PCT WO 01/25151 published Apr. 12, 2001 (staged acid addition), PCT WO 01/60746 published Aug. 23, 2001 (silicon oil), U.S. patent application Ser. No. 09/929,949 filed Aug. 15, 2001 (cooling molecular sieve), U.S. patent application Ser. No. 09/615,526 filed Jul. 13, 2000 (metal impregnation including copper), U.S. patent application Ser. No. 09/672,469 filed Sep. 28, 2000 (conductive microfilter), and U.S. patent application Ser. No. 09/754,812 filed Jan. 4, 2001 (freeze drying the molecular sieve), which are all herein fully incorporated by reference.

In one preferred embodiment, when a templating agent is used in the synthesis of a molecular sieve, it is preferred that the templating agent is substantially, preferably completely, removed after crystallization by numerous well known techniques, for example, heat treatments such as calcination. Calcination involves contacting the molecular sieve containing the templating agent with a gas, preferably containing oxygen, at any desired concentration at an elevated temperature sufficient to either partially or completely decompose and oxidize the templating agent.

Molecular sieve have either a high silicon (Si) to aluminum (Al) ratio or a low silicon to aluminum ratio, however, a low Si/Al ratio is preferred for SAPO synthesis. In one embodiment, the molecular sieve has a Si/Al ratio less than 0.65, preferably less than 0.40, more preferably less than 0.32, and most preferably less than 0.20. In another embodiment the molecular sieve has a Si/Al ratio in the range of from about 0.65 to about 0.10, preferably from about 0.40 to about 0.10, more preferably from about 0.32 to about 0.10, and more preferably from about 0.32 to about 0.15.

The pH of a reaction mixture containing at a minimum a silicon-, aluminum-, and/or phosphorous-composition, and a templating agent, should be in the range of from 2 to 10, preferably in the range of from 4 to 9, and most preferably in the range of from 5 to 8.

Group 3 Metal Oxides and Oxides of the Lanthanide or Actinide Series

The Group 3 metal oxides and oxides of the Lanthanide or Actinide series of the invention are those metal oxides, different from typical binders and/or matrix materials, that, when used in combination with a molecular sieve, provide benefits in catalytic conversion processes. Preferred active metal oxides are those metal oxides having a Group 3 metal, such as scandium, yttrium and lanthanum, or a metal from the Lanthanide or Actinide series, such as cerium, praseodymium, neodymium, samarium, europium, gadolinium, terbium, dysprosium, holmium, erbium, thulium, ytterbium, lutetium and thorium. The most preferred active metal oxides are scandium oxide, lanthanum oxide, yttrium oxide, cerium oxide, praseodymium oxide, neodymium oxide or mixtures thereof.

While there are many different benefits in catalytic conversion processes, one of the most desirable is an extension of the catalyst composition life. Quantification of the extension in the catalyst composition life is determined by the Lifetime Enhancement Index (LEI) as defined by the following equation:

$$LEI = \frac{\text{Lifetime of Catalyst in Combination with Active Metal Oxide(s)}}{\text{Lifetime of Catalyst}}$$

where the lifetime of the catalyst or catalyst composition, is measured in the same process under the same conditions, and is the cumulative amount of feedstock processed per gram of catalyst composition until the conversion of feedstock by the catalyst composition falls below some defined level, for example 10%. A mixture containing an inactive metal oxide will have little to no effect on the lifetime of the catalyst composition, or will shorten the lifetime of the catalyst composition, and will therefore have a LEI less than or equal to 1. Active metal oxides of the invention are those Group 3 metal oxides, including oxides of the Lanthanide and Actinide series that when used in combination with a molecular sieve, provide a molecular sieve catalyst composition that has a LEI greater than 1. By definition, a molecular sieve catalyst composition that has not been combined with an active metal oxide will have a LEI equal to 1.0.

In one embodiment, the active Group 3 metal oxide and/or the active oxides of the Lanthanide and Actinide series when combined with a molecular sieve enhances the lifetime of the molecular sieve in a conversion process of a feedstock comprising methanol, preferably into one or more olefin(s). In another embodiment, the molecular sieve composition, molecular sieve catalyst composition, and formulated molecular sieve catalyst composition of the invention, each containing an active metal oxide, will have a LEI greater than 1. In a preferred embodiment, the LEI of the molecular sieve composition, molecular sieve catalyst composition, or formulated molecular sieve catalyst composition, all containing one or more Group 3 metal oxides and/or one or more active oxides of the Lanthanide and Actinide series is greater than 1.1, preferably greater than 1.3, more preferably greater than 1.5, even more preferably greater than 1.7 and most preferably greater than 2. In an alternative embodiment, the LEI of the molecular sieve composition, molecular sieve catalyst composition, or formulated molecular sieve catalyst composition, all containing at least one active Group 3 metal oxide and/or at least one active oxide of the Lanthanide and Actinide series is in the range of from greater than 1 to 30, more preferably in the range of from about 1.2 to 25, and most preferably in the range of from about 1.5 to about 20.

In one embodiment, the active Group 3 metal oxides of the invention, including oxides of the Lanthanide and Actinide series elements, are non-acidic or basic metal oxides.

In another embodiment, when combining more than one metal oxide of the invention with a molecular sieve, the metal oxides are each made separately and then contacted together, or pre-combined, with the molecular sieve, or alternatively, each metal oxide is contacted sequentially with the molecular sieve. In an embodiment, the metal oxides of the invention are mixed together in a slurry or hydrated state or in a substantially dry or dried state, preferably the metal oxides are contacted in a hydrated state.

The metal oxides of the invention are prepared using a variety of methods. It is preferable that the metal oxide is made from metal oxide precursors, such as metal salts. Other suitable sources of the metal oxides include compounds that form these metal oxides during calcination, such as oxychlorides and nitrates. Alkoxides are also sources of the metal oxides of the invention, for example yttrium n-propoxide.

In one embodiment, a preferred Group 3 metal oxide or oxide of the Lanthanide or Actinide series is hydrothermally treated under conditions that include a temperature of at least 80° C., preferably at least 100° C. The hydrothermal treatment typically takes place in a sealed vessel at greater than atmospheric pressure. However, a preferred mode of treatment involves the use of an open vessel under reflux conditions. Agitation of the Group 3 metal oxide or the oxide of the Lanthanide or Actinide series in the liquid medium, for example, by the action of refluxing liquid and/or stirring, promotes the effective interaction of the oxide with the liquid medium. The duration of the contact of the oxide with the liquid medium is preferably at least 1 hour, preferably at least 8 hours. The liquid medium for this treatment preferably has a pH of about 7 or greater, preferably 9 or greater. Non-limiting examples of suitable liquid media include water, hydroxide solutions (including hydroxides of $NH_4^+$, $Na^+$, $K^+$, $Mg^{2+}$, and $Ca^{2+}$), carbonate and bicarbonate solutions (including carbonates and bicarbonates of $NH_4^+$, $Na^+$, $K^+$, $Mg^{2+}$, and $Ca^{2+}$), pyridine and its derivatives, and alkyl/hydroxyl amines.

In yet another embodiment, the active Group 3 metal oxide or the active oxide of the Lanthanide or Actinide series is prepared, for example, by first preparing a liquid solution comprising a source of a Group 3 metal or combination of Group 3 metals or one or more elements of the Lanthanide or Actinide series of elements. Suitable sources for the Group 3 metal or the Lanthanide or Actinide series element include, but are not limited to, salts containing a Group 3 metal or Lanthanide or Actinide element, such as nitrates, sulfates and halides.

This solution containing a source of a Group 3 metal or a source of a Lanthanide or Actinide series element, or combinations thereof is then subjected to conditions sufficient to cause precipitation of the solid metal oxide, such as by the addition of a precipitating reagent to the solution. For example, the precipitating agent(s) preferably is a base such as sodium hydroxide or ammonium hydroxide. Water is a preferred solvent for these solutions. The temperature at which the liquid medium(s) is maintained during the precipitation is preferably less than about 200° C., preferably in the range of from about 0° C. to about 200° C. This liquid medium(s) is preferably maintained at an ambient temperature, for example room temperature or the liquid is cooled or heated. A particular range of temperatures for precipitation is from about 20° C. to about 100° C. The resulting gel is preferably then hydrothermally treated at temperatures of at least 80° C., preferably at least 100° C. The hydrothermal treatment typically takes place in a sealed vessel at greater than atmospheric pressure. The gel, in one embodiment, is hydrothermally treated for up to 10 days, preferably up to 5 days, most preferably up to 3 days. The resulting material is then recovered, for example by filtration or centrifugation, and washed and dried. The resulting material is preferably then calcined, preferably in an oxidizing atmosphere, at a temperature of at least 400° C., preferably at least 500° C., and more preferably from about 600° C. to about 900° C., and most preferably from about 600° C. to about 800° C. The calcination time is preferably up to 48 hours, preferably for about 0.5 to 24 hours, and more preferably for about 1.0 to 10 hours.

Molecular Sieve Composition

The molecular sieve composition of the invention includes any one of the molecular sieves previously described and one or more of the Group 3 metal oxides and/or one or more oxide(s) of a Lanthanide or Actinide series element described above. Most preferably, the molecular sieves are those resulting from the synthesis mixture of phosphorous-, aluminum-, and/or silicon-containing components, preferably while stirring and/or agitation and/or seeding with a crystalline material, optionally in the presence of an alkali metal, in a solvent such as water, and one or more templating agents, to form a synthesis mixture that is then heated under crystallization conditions of pressure and temperature as described in U.S. Pat. Nos. 4,440,871, 4,861,743, 5,096,684, and 5,126,308, which are all herein fully incorporated by reference.

In the more preferred embodiment, the molecular sieve is first formed and is then combined with an active Group 3 metal oxide or an active oxide of a Lanthanide or Actinide series element, preferably in a substantially dry, dried, or calcined state, most preferably the molecular sieve and active Group 3 metal oxide or active oxide of a Lanthanide or Actinide series element are physically mixed in their calcined state to form the preferred molecular sieve composition of the invention. Without being bound by any particular theory, it is believed that intimate mixing of the molecular sieve and the active Group 3 metal oxide or the active oxide of a Lanthanide or Actinide series element improve conversion processes using the molecular sieve composition and catalyst composition of the invention. Intimate mixing may be achieved by any method known in the art, such as mixing with a mixer muller, drum mixer, ribbon/paddle blender, kneader, or the like.

In one embodiment, the molecular sieve composition or molecular sieve catalyst composition has a weight ratio of the molecular sieve to the active Group 3 metal oxide or the active oxide of a Lanthanide or Actinide series element in the range of from 5 weight percent to 800 weight percent, particularly in the range from 10 weight percent to 600 weight percent, more particularly from 20 weight percent to 500 weight percent, and most preferably from 30 weight percent to 400 weight percent.

Method for Making Molecular Sieve Catalyst Compositions

Once the molecular sieve is synthesized or the molecular sieve composition is made, depending on the requirements of the particular conversion process, the molecular sieve or the molecular sieve composition is then formulated into a molecular sieve catalyst composition, particularly for commercial use. A molecular sieve catalyst composition is made or formulated by combining a molecular sieve synthesized above or a molecular sieve composition above, with a binder and/or a matrix material. In one embodiment, where the molecular sieve synthesized above is formulated into a molecular sieve catalyst composition, the active Group 3 metal oxide or the active oxide of a Lanthanide or Actinide series element is then combined with the formulated molecular sieve catalyst composition. It is also an embodiment of the invention that a first formulated molecular sieve catalyst is combined with an active Group 3 metal oxide or an active oxide of a Lanthanide or Actinide series element that is then formulated together into a second formulated molecular sieve catalyst composition. These formulated molecular sieve catalyst composition are then formed into useful shape and sized particles by well-known techniques such as spray drying, pelletizing, extrusion, and the like.

There are many different binders that are useful in forming molecular sieve catalyst compositions or formulated molecular sieve catalyst compositions. In one preferred embodiment, the binder is different from at least one of, most preferably any, of the Group 3 metal oxides or the oxides of a Lanthanide or Actinide series element discussed above. Non-limiting examples of binders that are useful alone or in combination include various types of hydrated alumina, silicas, and/or other inorganic oxide sol. One preferred alumina containing sol is aluminum chlorhydrol or chlorhydrate. The inorganic oxide sol acts like glue binding the synthesized molecular sieves and other materials such as the matrix together, particularly after thermal treatment. Upon heating, the inorganic oxide sol, preferably having a low viscosity, is converted into an inorganic oxide matrix component. For example, an alumina sol will convert to an aluminum oxide matrix following heat treatment.

Aluminum chlorhydrate, a hydroxylated aluminum based sol containing a chloride counter ion, has the general formula of $Al_mO_n(OH)_oCl_p \cdot x(H_2O)$ wherein m is 1 to 20, n is 1 to 8, o is 5 to 40, p is 2 to 15, and x is 0 to 30. In one embodiment, the binder is $Al_{13}O_4(OH)_{24}Cl_7 \cdot 12(H_2O)$ as is described in G. M. Wolterman, et al., Stud. Surf. Sci. and Catal., 76, pages 105–144 (1993), which is herein incorporated by reference. In another embodiment, one or more binders are combined with one or more other non-limiting examples of alumina materials such as aluminum oxyhydroxide, γ-alumina, boehmite, diaspore, and transitional aluminas such as α-alumina, β-alumina, γ-alumina, δ-alumina, ε-alumina, κ-alumina, and ρ-alumina, aluminum trihydroxide, such as gibbsite, bayerite, nordstrandite, doyelite, and mixtures thereof.

In another embodiment, the binders are alumina sols, predominantly comprising aluminum oxide, optionally including some silicon. In yet another embodiment, the binders are peptized alumina made by treating alumina hydrates such as pseudobohemite, with an acid, preferably an acid that does not contain a halogen, to prepare sols or aluminum ion solutions. Non-limiting examples of commercially available colloidal alumina sols include Nalco 8676 available from Nalco Chemical Co., Naperville, Ill., and Nyacol available from The PQ Corporation, Valley Forge, Pa.

Preferably, the molecular sieve compositions described above are combined with one or more matrix material(s). In the preferred embodiment, the matrix material is different from the Group 3 metal oxide or the oxide of a Lanthanide or Actinide series element. Matrix materials are typically effective in reducing overall catalyst cost, act as thermal sinks assisting in shielding heat from the catalyst composition for example during regeneration, densifying the catalyst composition, and increasing catalyst strength such as crush strength and attrition resistance.

Non-limiting examples of matrix materials include one or more of: non-active metal oxides including magnesia, beryllia, quartz, silica or sols, and mixtures thereof, for example silica-magnesia, silica-zirconia, silica-titania, silica-alumina and silica-alumina-thoria. In an embodiment, matrix materials are natural clays such as those from the families of montmorillonite and kaolin. These natural clays include sabbentonites and those kaolins known as, for example, Dixie, McNamee, Georgia and Florida clays. Non-limiting examples of other matrix materials include: haloysite, kaolinite, dickite, nacrite, or anauxite. In one embodiment, the matrix material, preferably any of the clays, are subjected to well known modification processes such as calcination and/or acid treatment and/or chemical treatment.

In one preferred embodiment, the matrix material is a clay or a clay-type composition, preferably the clay or clay-type composition having a low iron or titania content, and most preferably the matrix material is kaolin. Kaolin has been found to form a pumpable, high solid content slurry, it has a low fresh surface area, and it packs together easily due to its platelet structure. A preferred average particle size of the matrix material, most preferably kaolin, is from about 0.1 μm to about 0.6 μm with a D90 particle size distribution of less than about 1 μm.

In one embodiment, the binder, the molecular sieve composition and the matrix material are combined in the presence of a liquid to form a molecular sieve catalyst composition, where the amount of binder is from about 2% by weight to about 30% by weight, preferably from about 5% by weight to about 20% by weight, and more preferably from about 7% by weight to about 15% by weight, based on the total weight of the binder, the molecular sieve and matrix material, excluding the liquid (after calcination).

In another embodiment, the weight ratio of the binder to the matrix material used in the formation of the molecular sieve catalyst composition is from 0:1 to 1:15, preferably 1:15 to 1:5, more preferably 1:10 to 1:4, and most preferably 1:6 to 1:5. It has been found that a higher sieve content, lower matrix content, increases the molecular sieve catalyst composition performance, however, lower sieve content, higher matrix material, improves the attrition resistance of the composition.

Upon combining the molecular sieve composition and the matrix material, optionally with a binder, in a liquid to form a slurry, mixing, preferably rigorous mixing is needed to produce a substantially homogeneous mixture containing the molecular sieve composition. Non-limiting examples of suitable liquids include one or a combination of water, alcohol, ketones, aldehydes, and/or esters. The most preferred liquid is water. In one embodiment, the slurry is colloid-milled for a period of time sufficient to produce the desired slurry texture, sub-particle size, and/or sub-particle size distribution.

The molecular sieve composition and matrix material, and the optional binder, are in the same or different liquid, and are combined in any order, together, simultaneously, sequentially, or a combination thereof. In the preferred embodiment, the same liquid, preferably water is used. The molecular sieve composition, matrix material, and optional binder, are combined in a liquid as solids, substantially dry or in a dried form, or as slurries, together or separately. If solids are added together as dry or substantially dried solids, it is preferable to add a limited and/or controlled amount of liquid.

In one embodiment, the slurry of the molecular sieve composition, binder and matrix materials is mixed or milled to achieve a sufficiently uniform slurry of sub-particles of the molecular sieve catalyst composition that is then fed to a forming unit that produces the molecular sieve catalyst composition. In a preferred embodiment, the forming unit is spray dryer. Typically, the forming unit is maintained at a temperature sufficient to remove most of the liquid from the slurry, and from the resulting molecular sieve catalyst composition. The resulting catalyst composition when formed in this way takes the form of microspheres.

When a spray drier is used as the forming unit, typically, the slurry of the molecular sieve composition and matrix material, and optionally a binder, is co-fed to the spray drying volume with a drying gas with an average inlet temperature ranging from 200° C. to 550° C., and a combined outlet temperature ranging from 100° C. to about 225° C. In an embodiment, the average diameter of the spray dried formed catalyst composition is from about 40 µm to about 300 µm, preferably from about 50 µm to about 250 µm, more preferably from about 50 µm to about 200 µm, and most preferably from about 65 µm to about 90 µm.

Other methods for forming a molecular sieve catalyst composition is described in U.S. patent application Ser. No. 09/617,714 filed Jul. 17, 2000 (spray drying using a recycled molecular sieve catalyst composition), which is herein incorporated by reference.

In another embodiment, the molecular sieve catalyst composition or formulated molecular sieve catalyst composition contains from about 1% to about 80%, more preferably from about 5% to about 60%, and most preferably from about 5% to about 50%, by weight of the molecular sieve based on the total weight of the molecular sieve catalyst composition or formulated molecular sieve catalyst composition.

In another embodiment, the weight percent of binder in or on the spray dried molecular sieve catalyst composition based on the total weight of the binder, molecular sieve composition, matrix material and active Group 3 metal oxide(s) is from about 2% by weight to about 30% by weight, preferably from about 5% by weight to about 20% by weight, and more preferably from about 7% by weight to about 15% by weight.

Once the molecular sieve catalyst composition is formed in a substantially dry or dried state, to further harden and/or activate the formed catalyst composition, a heat treatment such as calcination, at an elevated temperature is usually performed. A conventional calcination environment is air that typically includes a small amount of water vapor. Typical calcination temperatures are in the range from about 400° C. to about 1,000° C., preferably from about 500° C. to about 800° C., and most preferably from about 550° C. to about 700° C., preferably in a calcination environment such as air, nitrogen, helium, flue gas (combustion product lean in oxygen), or any combination thereof.

In a preferred embodiment, the molecular sieve catalyst composition is heated in nitrogen at a temperature of from about 600° C. to about 700° C. Heating is carried out for a period of time typically from 30 minutes to 15 hours, preferably from 1 hour to about 10 hours, more preferably from about 1 hour to about 5 hours, and most preferably from about 2 hours to about 4 hours.

In one embodiment, the molecular sieve catalyst composition or formulated molecular sieve catalyst composition of the invention has a density in the range of from 0.5 g/cc to 5 g/cc, preferably from in the range of from 0.6 g/cc to 5 g/cc, more preferably in the range of from 0.7 g/cc to 4 g/cc, and most preferably in the range of from 0.8 g/cc to 3 g/cc.

Process for Using the Molecular Sieve Catalyst Compositions

The molecular sieve compositions and catalyst compositions described above are useful in a variety of processes including: cracking, of for example a naphtha feed to light olefin(s) (U.S. Pat. No. 6,300,537) or higher molecular weight (MW) hydrocarbons to lower MW hydrocarbons; hydrocracking, of for example heavy petroleum and/or cyclic feedstock; isomerization, of for example aromatics such as xylene, polymerization, of for example one or more olefin(s) to produce a polymer product; reforming; hydrogenation; dehydrogenation; dewaxing, of for example hydrocarbons to remove straight chain paraffins; absorption, of for example alkyl aromatic compounds for separating out isomers thereof; alkylation, of for example aromatic hydrocarbons such as benzene and alkyl benzene, optionally with propylene to produce cumeme or with long chain olefins; transalkylation, of for example a combination of aromatic and polyalkylaromatic hydrocarbons; dealkylation; hydrodecylization; disproportionation, of for example toluene to make benzene and paraxylene; oligomerization, of for example straight and branched chain olefin(s); and dehydrocyclization.

Preferred processes are conversion processes including: naphtha to highly aromatic mixtures; light olefin(s) to gasoline, distillates and lubricants; oxygenates to olefin(s); light paraffins to olefins and/or aromatics; and unsaturated hydrocarbons (ethylene and/or acetylene) to aldehydes for conversion into alcohols, acids and esters. The most preferred process of the invention is a process directed to the conversion of a feedstock comprising one or more oxygenates to one or more olefin(s).

The molecular sieve compositions and molecular sieve catalyst compositions and formulated versions thereof described above are particularly useful in conversion processes of different feedstock. Typically, the feedstock contains one or more aliphatic-containing compounds that include alcohols, amines, carbonyl compounds for example aldehydes, ketones and carboxylic acids, ethers, halides, mercaptans, sulfides, and the like, and mixtures thereof. The aliphatic moiety of the aliphatic-containing compounds typically contains from 1 to about 50 carbon atoms, preferably from 1 to 20 carbon atoms, more preferably from 1 to 10 carbon atoms, and most preferably from 1 to 4 carbon atoms.

Non-limiting examples of aliphatic-containing compounds include: alcohols such as methanol and ethanol, alkyl-mercaptans such as methyl mercaptan and ethyl mercaptan, alkyl-sulfides such as methyl sulfide, alkyl-amines such as methyl amine, alkyl-ethers such as dimethyl ether, diethyl ether and methylethyl ether, alkyl-halides such as methyl chloride and ethyl chloride, alkyl ketones such as dimethyl ketone, formaldehydes, and various acids such as acetic acid.

In a preferred embodiment of the process of the invention, the feedstock contains one or more oxygenates, more specifically, one or more organic compound(s) containing at least one oxygen atom. In the most preferred embodiment of the process of invention, the oxygenate in the feedstock is one or more alcohol(s), preferably aliphatic alcohol(s) where the aliphatic moiety of the alcohol(s) has from 1 to 20 carbon atoms, preferably from 1 to 10 carbon atoms, and most preferably from 1 to 4 carbon atoms. The alcohols useful as feedstock in the process of the invention include lower straight and branched chain aliphatic alcohols and their unsaturated counterparts.

Non-limiting examples of oxygenates include methanol, ethanol, n-propanol, isopropanol, methyl ethyl ether, dimethyl ether, diethyl ether, di-isopropyl ether, formaldehyde, dimethyl carbonate, dimethyl ketone, acetic acid, and mixtures thereof.

In the most preferred embodiment, the feedstock is selected from one or more of methanol, ethanol, dimethyl ether, diethyl ether or a combination thereof, more preferably methanol and dimethyl ether, and most preferably methanol.

The various feedstocks discussed above, particularly a feedstock containing an oxygenate, more particularly a feedstock containing an alcohol, is converted primarily into one or more olefin(s). The olefin(s) or olefin monomer(s) produced from the feedstock typically have from 2 to 30 carbon atoms, preferably 2 to 8 carbon atoms, more preferably 2 to 6 carbon atoms, still more preferably 2 to 4 carbons atoms, and most preferably ethylene and/or propylene.

Non-limiting examples of olefin monomer(s) include ethylene, propylene, butene-1, pentene-1,4-methyl-pentene-1, hexene-1, octene-1 and decene-1, preferably ethylene, propylene, butene-1, pentene-1,4-methyl-pentene-1, hexene-1, octene-1 and isomers thereof. Other olefin monomer(s) include unsaturated monomers, diolefins having 4 to 18 carbon atoms, conjugated or nonconjugated dienes, polyenes, vinyl monomers and cyclic olefins.

In the most preferred embodiment, the feedstock, preferably of one or more oxygenates, is converted in the presence of a molecular sieve catalyst composition into olefin(s) having 2 to 6 carbons atoms, preferably 2 to 4 carbon atoms. Most preferably, the olefin(s), alone or combination, are converted from a feedstock containing an oxygenate, preferably an alcohol, most preferably methanol, to the preferred olefin(s) ethylene and/or propylene.

The are many processes used to convert feedstock into olefin(s) including various cracking processes such as steam cracking, thermal regenerative cracking, fluidized bed cracking, fluid catalytic cracking, deep catalytic cracking, and visbreaking.

The most preferred process is generally referred to as gas-to-olefins (GTO) or alternatively, methanol-to-olefins (MTO). In a MTO process, typically an oxygenated feedstock, most preferably a methanol containing feedstock, is converted in the presence of a molecular sieve composition or catalyst composition thereof into one or more olefin(s), preferably and predominantly, ethylene and/or propylene, often referred to as light olefin(s).

In one embodiment of the process for conversion of a feedstock, preferably a feedstock containing one or more oxygenates, the amount of olefin(s) produced based on the total weight of hydrocarbon produced is greater than 50 weight percent, preferably greater than 60 weight percent, more preferably greater than 70 weight percent, and most preferably greater than 75 weight percent. In another embodiment of the process for conversion of one or more oxygenates to one or more olefin(s), the amount of ethylene and/or propylene produced based on the total weight of hydrocarbon product produced is greater than 65 weight percent, preferably greater than 70 weight percent, more preferably greater than 75 weight percent, and most preferably greater than 78 weight percent.

In another embodiment of the process for conversion of one or more oxygenates to one or more olefin(s), the amount ethylene produced in weight percent based on the total weight of hydrocarbon product produced, is greater than 30 weight percent, more preferably greater than 35 weight percent, and most preferably greater than 40 weight percent. In yet another embodiment of the process for conversion of one or more oxygenates to one or more olefin(s), the amount of propylene produced in weight percent based on the total weight of hydrocarbon product produced is greater than 20 weight percent, preferably greater than 25 weight percent, more preferably greater than 30 weight percent, and most preferably greater than 35 weight percent.

In the most preferred embodiments, the molecular sieve catalyst composition comprises a silicoaluminophosphate and an active Group 3 metal oxide or oxide of the Lanthanide or Actinide series elements and the oxygenates include methanol and/or dimethyl ether.

In another embodiment, in a process for conversion an oxygenate comprising methanol and dimethylether to ethylene and propylene in the presence of a molecular sieve and an active metal oxide, preferably a molecular sieve composition of the two, most preferably a molecular sieve catalyst composition of the two, the production of ethane and propane is reduced by greater than 10%, preferably greater than 20%, more preferably greater than 30%, and most preferably in the range of from about 30% to 50% compared to the molecular sieve alone or its catalyst composition at the same conversion conditions.

The feedstock, in one embodiment, contains one or more diluent(s), typically used to reduce the concentration of the feedstock, and are generally non-reactive to the feedstock or molecular sieve catalyst composition. Non-limiting examples of diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred.

The diluent, water, is used either in a liquid or a vapor form, or a combination thereof. The diluent is either added directly to a feedstock entering into a reactor or added directly into a reactor, or added with a molecular sieve catalyst composition.

The process for converting a feedstock, especially a feedstock containing one or more oxygenates, in the presence of a molecular sieve catalyst composition of the invention, is carried out in a reaction process in a reactor, where the process is a fixed bed process, a fluidized bed process (includes a turbulent bed process), preferably a continuous fluidized bed process, and most preferably a continuous high velocity fluidized bed process.

The reaction processes can take place in a variety of catalytic reactors such as hybrid reactors that have a dense bed or fixed bed reaction zones and/or fast fluidized bed reaction zones coupled together, circulating fluidized bed reactors, riser reactors, and the like. Suitable conventional reactor types are described in for example U.S. Pat. No. 4,076,796, U.S. Pat. No. 6,287,522 (dual riser), and *Fluidization Engineering*, D. Kunii and O. Levenspiel, Robert E. Krieger Publishing Company, New York, N.Y. 1977, which are all herein fully incorporated by reference.

The preferred reactor type are riser reactors generally described in *Riser Reactor, Fluidization and Fluid-Particle Systems*, pages 48 to 59, F. A. Zenz and D. F. Othmo, Reinhold Publishing Corporation, New York, 1960, and U.S. Pat. No. 6,166,282 (fast-fluidized bed reactor), and U.S. patent application Ser. No. 09/564,613 filed May 4, 2000 (multiple riser reactor), which are all herein fully incorporated by reference.

In the preferred embodiment, a fluidized bed process or high velocity fluidized bed process includes a reactor system, a regeneration system and a recovery system.

The reactor system preferably is a fluid bed reactor system having a first reaction zone within one or more riser reactor(s) and a second reaction zone within at least one disengaging vessel, preferably comprising one or more cyclones. In one embodiment, the one or more riser reactor(s) and disengaging vessel is contained within a single reactor vessel. Fresh feedstock, preferably containing one or more oxygenates, optionally with one or more diluent(s), is fed to the one or more riser reactor(s) in which a molecular sieve catalyst composition or coked version thereof is introduced. In one embodiment, the molecular sieve catalyst composition or coked version thereof is contacted with a liquid or gas, or combination thereof, prior to being introduced to the riser reactor(s), preferably the liquid is water or methanol, and the gas is an inert gas such as nitrogen.

In an embodiment, the amount of fresh feedstock fed separately or jointly with a vapor feedstock, to a reactor system is in the range of from 0.1 weight percent to about 85 weight percent, preferably from about 1 weight percent to about 75 weight percent, more preferably from about 5 weight percent to about 65 weight percent based on the total weight of the feedstock including any diluent contained therein. The liquid and vapor feedstocks are preferably the same composition, or contain varying proportions of the same or different feedstock with the same or different diluent.

The feedstock entering the reactor system is preferably converted, partially or fully, in the first reactor zone into a gaseous effluent that enters the disengaging vessel along with a coked molecular sieve catalyst composition. In the preferred embodiment, cyclone(s) within the disengaging vessel are designed to separate the molecular sieve catalyst composition, preferably a coked molecular sieve catalyst composition, from the gaseous effluent containing one or more olefin(s) within the disengaging zone. Cyclones are preferred, however, gravity effects within the disengaging vessel will also separate the catalyst compositions from the gaseous effluent. Other methods for separating the catalyst compositions from the gaseous effluent include the use of plates, caps, elbows, and the like.

In one embodiment of the disengaging system, the disengaging system includes a disengaging vessel, typically a lower portion of the disengaging vessel is a stripping zone. In the stripping zone the coked molecular sieve catalyst composition is contacted with a gas, preferably one or a combination of steam, methane, carbon dioxide, carbon monoxide, hydrogen, or an inert gas such as argon, preferably steam, to recover adsorbed hydrocarbons from the coked molecular sieve catalyst composition that is then introduced to the regeneration system.

The conversion temperature employed in the conversion process, specifically within the reactor system, is in the range of from about 200° C. to about 1000° C., preferably from about 250° C. to about 800° C., more preferably from about 250° C. to about 750° C., yet more preferably from about 300° C. to about 650° C., yet even more preferably from about 350° C. to about 600° C. most preferably from about 350° C. to about 550° C.

The conversion pressure employed in the conversion process, specifically within the reactor system, varies over a wide range including autogenous pressure. The conversion pressure is based on the partial pressure of the feedstock exclusive of any diluent therein. Typically the conversion pressure employed in the process is in the range of from about 0.1 kPaa to about 5 MPaa, preferably from about 5 kPaa to about 1 MPaa, and most preferably from about 20 kPaa to about 500 kPaa.

The weight hourly space velocity (WHSV), particularly in a process for converting a feedstock containing one or more oxygenates in the presence of a molecular sieve catalyst composition within a reaction zone, is defined as the total weight of the feedstock excluding any diluents to the reaction zone per hour per weight of molecular sieve in the molecular sieve catalyst composition in the reaction zone. The WHSV is maintained at a level sufficient to keep the catalyst composition in a fluidized state within a reactor.

Typically, the WHSV ranges from about 1 $hr^{-1}$ to about 5000 $hr^{-1}$, preferably from about 2 $hr^{-1}$ to about 3000 $hr^{-1}$, more preferably from about 5 $hr^{-1}$ to about 1500 $hr^{-1}$, and most preferably from about 10 $hr^{-1}$ to about 1000 $hr^{-1}$. In one preferred embodiment, the WHSV is greater than 20 $hr^{-1}$, preferably the WHSV for conversion of a feedstock containing methanol and dimethyl ether is in the range of from about 20 $hr^{-1}$ to about 300 $hr^{-1}$.

The superficial gas velocity (SGV) of the feedstock including diluent and reaction products within the reactor system is preferably sufficient to fluidize the molecular sieve catalyst composition within a reaction zone in the reactor. The SGV in the process, particularly within the reactor system, more particularly within the riser reactor(s), is at least 0.1 meter per second (m/sec), preferably greater than 0.5 m/sec, more preferably greater than 1 m/sec, even more preferably greater than 2 m/sec, yet even more preferably greater than 3 m/sec, and most preferably greater than 4 m/sec. See for example U.S. patent application Ser. No. 09/708,753 filed Nov. 8, 2000, which is herein incorporated by reference.

The coked molecular sieve catalyst composition is withdrawn from the disengaging vessel and introduced to the regeneration system. The regeneration system comprises a regenerator where the coked catalyst composition is contacted with a regeneration medium, preferably a gas containing oxygen, under general regeneration conditions of temperature, pressure and residence time.

Non-limiting examples of the regeneration medium include one or more of oxygen, $O_3$, $SO_3$, $N_2O$, NO, $NO_2$, $N_2O_5$, air, air diluted with nitrogen or carbon dioxide, oxygen and water (U.S. Pat. No. 6,245,703), carbon monoxide and/or hydrogen. The regeneration conditions are those capable of burning coke from the coked catalyst composition, preferably to a level less than 0.5 weight percent based on the total weight of the coked molecular sieve catalyst composition entering the regeneration system. The coked molecular sieve catalyst composition withdrawn from the regenerator forms a regenerated molecular sieve catalyst composition.

The regeneration temperature is in the range of from about 200° C. to about 1500° C., preferably from about 300° C. to about 1000° C., more preferably from about 450° C. to about 750° C., and most preferably from about 550° C. to 700° C. The regeneration pressure is in the range of from about 15 psia (103 kPaa) to about 500 psia (3448 kPaa), preferably from about 20 psia (138 kPaa) to about 250 psia (1724 kPaa), more preferably from about 25 psia (172 kPaa) to about 150 psia (1034 kPaa), and most preferably from about 30 psia (207 kPaa) to about 60 psia (414 kPaa).

The preferred residence time of the molecular sieve catalyst composition in the regenerator is in the range of from about one minute to several hours, most preferably about one minute to 100 minutes, and the preferred volume of oxygen in the gas is in the range of from about 0.01 mole percent to about 5 mole percent based on the total volume of the gas.

In an embodiment, a portion of the molecular sieve catalyst composition from the regenerator is returned directly to the one or more riser reactor(s), or indirectly, by pre-contacting with the feedstock, or contacting with fresh molecular sieve catalyst composition, or contacting with a regenerated molecular sieve catalyst composition or a cooled regenerated molecular sieve catalyst composition described below.

The burning of coke is an exothermic reaction, and in an embodiment, the temperature within the regeneration system is controlled by various techniques in the art including feeding a cooled gas to the regenerator vessel, operated either in a batch, continuous, or semi-continuous mode, or a combination thereof. A preferred technique involves withdrawing the regenerated molecular sieve catalyst composition from the regeneration system and passing the regenerated molecular sieve catalyst composition through a catalyst cooler that forms a cooled regenerated molecular sieve catalyst composition. The catalyst cooler, in an embodiment, is a heat exchanger that is located either internal or external to the regeneration system. Other methods for operating a regeneration system are in disclosed U.S. Pat. No. 6,290,916 (controlling moisture), which is herein fully incorporated by reference.

The regenerated molecular sieve catalyst composition withdrawn from the regeneration system, preferably from the catalyst cooler, is combined with a fresh molecular sieve catalyst composition and/or re-circulated molecular sieve catalyst composition and/or feedstock and/or fresh gas or liquids, and returned to the riser reactor(s). In another embodiment, the regenerated molecular sieve catalyst composition withdrawn from the regeneration system is returned to the riser reactor(s) directly, preferably after passing through a catalyst cooler. In one embodiment, a carrier, such as an inert gas, feedstock vapor, steam or the like, semi-continuously or continuously, facilitates the introduction of the regenerated molecular sieve catalyst composition to the reactor system, preferably to the one or more riser reactor(s).

By controlling the flow of the regenerated molecular sieve catalyst composition or cooled regenerated molecular sieve catalyst composition from the regeneration system to the reactor system, the optimum level of coke on the molecular sieve catalyst composition entering the reactor is maintained. There are many techniques for controlling the flow of a molecular sieve catalyst composition described in Michael Louge, *Experimental Techniques, Circulating Fluidized Beds*, Grace, Avidan and Knowlton, eds., Blackie, 1997 (336–337), which is herein incorporated by reference.

Coke levels on the molecular sieve catalyst composition is measured by withdrawing from the conversion process the molecular sieve catalyst composition at a point in the process and determining its carbon content. Typical levels of coke on the molecular sieve catalyst composition, after regeneration is in the range of from 0.01 weight percent to about 15 weight percent, preferably from about 0.1 weight percent to about 10 weight percent, more preferably from about 0.2 weight percent to about 5 weight percent, and most preferably from about 0.3 weight percent to about 2 weight percent based on the total weight of the molecular sieve and not the total weight of the molecular sieve catalyst composition.

The gaseous effluent is withdrawn from the disengaging system and is passed through a recovery system. There are many well known recovery systems, techniques and sequences that are useful in separating olefin(s) and purifying olefin(s) from the gaseous effluent. Recovery systems generally comprise one or more or a combination of a various separation, fractionation and/or distillation towers, columns, splitters, or trains, reaction systems such as ethylbenzene manufacture (U.S. Pat. No. 5,476,978) and other derivative processes such as aldehydes, ketones and ester manufacture (U.S. Pat. No. 5,675,041), and other associated equipment for example various condensers, heat exchangers, refrigeration systems or chill trains, compressors, knock-out drums or pots, pumps, and the like.

Non-limiting examples of these towers, columns, splitters or trains used alone or in combination include one or more of a demethanizer, preferably a high temperature demethanizer, a dethanizer, a depropanizer, a wash tower often referred to as a caustic wash tower and/or quench tower, absorbers, adsorbers, membranes, ethylene (C2) splitter, propylene (C3) splitter, butene (C4) splitter, and the like.

Various recovery systems useful for recovering predominately olefin(s), preferably prime or light olefin(s) such as ethylene, propylene and/or butene are described in U.S. Pat. No. 5,960,643 (secondary rich ethylene stream), U.S. Pat. Nos. 5,019,143, 5,452,581 and 5,082,481 (membrane separations), U.S. Pat. No. 5,672,197 (pressure dependent adsorbents), U.S. Pat. No. 6,069,288 (hydrogen removal), U.S. Pat. No. 5,904,880 (recovered methanol to hydrogen and carbon dioxide in one step), U.S. Pat. No. 5,927,063 (recovered methanol to gas turbine power plant), and U.S. Pat. No. 6,121,504 (direct product quench), U.S. Pat. No. 6,121,503 (high purity olefins without superfractionation), and U.S. Pat. No. 6,293,998 (pressure swing adsorption), which are all herein fully incorporated by reference.

Generally accompanying most recovery systems is the production, generation or accumulation of additional products, by-products and/or contaminants along with the preferred prime products. The preferred prime products, the light olefins, such as ethylene and propylene, are typically purified for use in derivative manufacturing processes such as polymerization processes. Therefore, in the most preferred embodiment of the recovery system, the recovery system also includes a purification system. For example, the light olefin(s) produced particularly in a MTO process are passed through a purification system that removes low levels of by-products or contaminants.

Non-limiting examples of contaminants and by-products include generally polar compounds such as water, alcohols, carboxylic acids, ethers, carbon oxides, sulfur compounds such as hydrogen sulfide, carbonyl sulfides and mercaptans, ammonia and other nitrogen compounds, arsine, phosphine and chlorides. Other contaminants or by-products include hydrogen and hydrocarbons such as acetylene, methyl acetylene, propadiene, butadiene and butyne.

Other recovery systems that include purification systems, for example for the purification of olefin(s), are described in *Kirk-Othmer Encyclopedia of Chemical Technology*, 4th Edition, Volume 9, John Wiley & Sons, 1996, pages 249–271 and 894–899, which is herein incorporated by reference. Purification systems are also described in for example, U.S. Pat. No. 6,271,428 (purification of a diolefin hydrocarbon stream), U.S. Pat. No. 6,293,999 (separating propylene from propane), and U.S. patent application Ser. No. 09/689,363 filed Oct. 20, 2000 (purge stream using hydrating catalyst), which is herein incorporated by reference.

Typically, in converting one or more oxygenates to olefin(s) having 2 or 3 carbon atoms, an amount of hydrocarbons, particularly olefin(s), especially olefin(s) having 4 or more carbon atoms, and other by-products are formed or produced. Included in the recovery systems of the invention are reaction systems for converting the products contained within the effluent gas withdrawn from the reactor or converting those products produced as a result of the recovery system utilized.

The effluent gas removed from a conversion process, particularly a MTO process, typically has a minor amount of hydrocarbons having 4 or more carbon atoms. The amount of hydrocarbons having 4 or more carbon atoms is typically in an amount less than 20 weight percent, preferably less than 10 weight percent, more preferably less than 5 weight percent, and most preferably less than 2 weight percent, based on the total weight of the effluent gas withdrawn from a MTO process, excluding water. In particular with a conversion process of oxygenates into olefin(s) utilizing a molecular sieve catalyst composition the resulting effluent gas typically comprises a majority of ethylene and/or propylene and a minor amount of four carbon and higher carbon number products and other by-products, excluding water.

Non-limiting examples of reaction systems include U.S. Pat. No. 5,955,640 (converting a four carbon product into butene-1), U.S. Pat. No. 4,774,375 (isobutane and butene-2 oligomerized to an alkylate gasoline), U.S. Pat. No. 6,049,017 (dimerization of n-butylene), U.S. Pat. Nos. 4,287,369 and 5,763,678 (carbonylation or hydroformulation of higher olefins with carbon dioxide and hydrogen making carbonyl compounds), U.S. Pat. No. 4,542,252 (multistage adiabatic process), U.S. Pat. No. 5,634,354 (olefin-hydrogen recovery), and Cosyns, J. et al., *Process for Upgrading C3, C4 and C5 Olefinic Streams*, Pet. & Coal, Vol. 37, No. 4 (1995) (dimerizing or oligomerizing propylene, butylene and pentylene), which are all herein fully incorporated by reference.

The preferred light olefin(s) produced by any one of the processes described above, preferably conversion processes, are high purity prime olefin(s) products that contains a single carbon number olefin in an amount greater than 80 percent, preferably greater than 90 weight percent, more preferably greater than 95 weight percent, and most preferably no less than about 99 weight percent, based on the total weight of the olefin.

In one embodiment, high purity prime olefin(s) are produced in the process of the invention at rate of greater than 5 kg per day, preferably greater than 10 kg per day, more preferably greater than 20 kg per day, and most preferably greater than 50 kg per day. In another embodiment, high purity ethylene and/or high purity propylene is produced by the process of the invention at a rate greater than 4,500 kg per day, preferably greater than 100,000 kg per day, more preferably greater than 500,000 kg per day, even more preferably greater than 1,000,000 kg per day, yet even more preferably greater than 1,500,000 kg per day, still even more preferably greater than 2,000,000 kg per day, and most preferably greater than 2,500,000 kg per day.

In an embodiment, an integrated process is directed to producing light olefin(s) from a hydrocarbon feedstock, preferably a hydrocarbon gas feedstock, more preferably methane and/or ethane. The first step in the process is passing the gaseous feedstock, preferably in combination with a water stream, to a syngas production zone to produce a synthesis gas (syngas) stream. Syngas production is well known, and typical syngas temperatures are in the range of from about 700° C. to about 1200° C. and syngas pressures are in the range of from about 2 MPa to about 100 MPa. Synthesis gas streams are produced from natural gas, petroleum liquids, and carbonaceous materials such as coal, recycled plastic, municipal waste or any other organic material, preferably synthesis gas stream is produced via steam reforming of natural gas.

Generally, a heterogeneous catalyst, typically a copper based catalyst, is contacted with a synthesis gas stream, typically carbon dioxide and carbon monoxide and hydrogen to produce an alcohol, preferably methanol, often in combination with water. In one embodiment, the synthesis gas stream at a synthesis temperature in the range of from about 150° C. to about 450° C. and at a synthesis pressure in the range of from about 5 MPa to about 10 MPa is passed through a carbon oxide conversion zone to produce an oxygenate containing stream.

This oxygenate containing stream, or crude methanol, typically contains the alcohol product and various other components such as ethers, particularly dimethyl ether, ketones, aldehydes, dissolved gases such as hydrogen methane, carbon oxide and nitrogen, and fuel oil. The oxygenate containing stream, crude methanol, in the preferred embodiment is passed through a well known purification processes, distillation, separation and fractionation, resulting in a purified oxygenate containing stream, for example, commercial Grade A and AA methanol.

The oxygenate containing stream or purified oxygenate containing stream, optionally with one or more diluents, is contacted with one or more molecular sieve catalyst composition described above in any one of the processes described above to produce a variety of prime products, particularly light olefin(s), ethylene and/or propylene. Non-limiting examples of this integrated process is described in EP-B-0 933 345, which is herein fully incorporated by reference.

In another more fully integrated process, optionally with the integrated processes described above, olefin(s) produced are directed to, in one embodiment, one or more polymerization processes for producing various polyolefins. (See for example U.S. patent application Ser. No. 09/615,376 filed Jul. 13, 2000, which is herein fully incorporated by reference.)

Polymerization processes include solution, gas phase, slurry phase and a high pressure processes, or a combination thereof. Particularly preferred is a gas phase or a slurry phase polymerization of one or more olefin(s) at least one of which is ethylene or propylene.

These polymerization processes utilize a polymerization catalyst that can include any one or a combination of the molecular sieve catalysts discussed above, however, the preferred polymerization catalysts are those Ziegler-Natta, Phillips-type, metallocene, metallocene-type and advanced polymerization catalysts, and mixtures thereof.

In preferred embodiment, the integrated process comprises a polymerizing process of one or more olefin(s) in the presence of a polymerization catalyst system in a polymerization reactor to produce one or more polymer products, wherein the one or more olefin(s) having been made by converting an alcohol, particularly methanol, using a molecular sieve catalyst composition. The preferred polymerization process is a gas phase polymerization process and at least one of the olefins(s) is either ethylene or propylene, and preferably the polymerization catalyst system is a supported metallocene catalyst system. In this embodiment, the supported metallocene catalyst system comprises a support, a metallocene or metallocene-type compound and an activator, preferably the activator is a non-coordinating anion or alumoxane, or combination thereof, and most preferably the activator is alumoxane.

The polymers produced by the polymerization processes described above include linear low density polyethylene, elastomers, plastomers, high density polyethylene, low density polyethylene, polypropylene and polypropylene copolymers. The propylene based polymers produced by the polymerization processes include atactic polypropylene, isotactic polypropylene, syndiotactic polypropylene, and propylene random, block or impact copolymers.

EXAMPLES

In order to provide a better understanding of the present invention including representative advantages thereof, the following examples are offered.

LEI is defined as the ratio of the lifetime of the molecular sieve composition, or the catalyst composition described below, to that of the molecular sieve in the absence of a metal oxide as discussed above. For the purpose of determining LEI, lifetime is defined as the cumulative oxygenate converted, preferably into one or more olefin(s) per gram of molecular sieve, wherein the conversion rate drops to about 10%. If the conversion has not reached 10% by the end of the experiment, lifetime is estimated by linear extrapolation based on the rate of decrease in conversion over the last two data points in the experiment. For the purposes of determining the LEI for the following examples in a preferred oxygenate conversion process, methanol is converted to one or more olefin(s) at 475° C., 25 psig (172 kPag) and a methanol weight hourly space velocity of 100 h$^{-1}$.

In Table 1, "Prime Olefin" is the sum of the selectivity to ethylene and propylene. The ratio "$C_2^=/C_3^=$" is the ratio of the ethylene to propylene selectivity weighted over the run. The "$C_3$ Purity" is calculated by dividing the propylene selectivity by the sum of the propylene and propane selectivity. In Table 2, the selectivity for methane, ethylene, ethane, propylene, propane, $C_4$'s and $C_5+$'s are average selectivity weighted over the run. Note that the $C_5+$'s consist only of $C_5$'s, $C_6$'s and $C_7$'s. The terms "$C_4$'s, $C_5+$, etc." refer to the number of carbons in the hydrocarbon. The selectivity values do not sum to 100% in the Tables because they have been corrected for coke as is well known.

Example A
Preparation of a Molecular Sieve

There are numerous methods well known for making molecular sieves. The following is an example preparation of a molecular sieve, particularly a silicoaluminophosphate molecular sieve, more particularly a SAPO-34, used in the compositions in these Examples, and referenced as MSA.

The MSA, SAPO-34 molecular sieve, was crystallized in the presence of tetraethyl ammonium hydroxide (R1) and dipropyl amine (R2) as the organic structure directing agents or templating agents. A mixture of the following mole ratio composition was prepared:

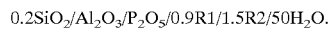

0.2SiO$_2$/Al$_2$O$_3$/P$_2$O$_5$/0.9R1/1.5R2/50H$_2$O.

An amount of Condea Pural SB was mixed with deionised water, to form a slurry. To this slurry was added an amount of phosphoric acid (85%). These additions were made with stirring to form a homogeneous mixture. To this homogeneous mixture Ludox AS40 (40% of SiO2) was added, followed by the addition of R1 with mixing to form a homogeneous mixture. To this homogeneous mixture R2 was added. This homogeneous mixture was then crystallized with agitation in a stainless steel autoclave by heating to 170° C. for 40 hours. This provided a slurry of the crystalline molecular sieve. The crystals were then separated from the mother liquor by filtration.

Formulation of a Molecular Sieve

There are a variety of methods for making or formulating a molecular sieve, a matrix material and a binder into a molecular sieve catalyst composition. The following is an example of making a molecular sieve catalyst composition. The crystalline molecular sieve prepared above was thoroughly mixed with water to form a molecular sieve slurry (A1). This slurry (A1) was then added to another slurry (A2) of a binder (for example, preferably aluminum chlorhydrol) and water, and was then again mixed thoroughly. As a final step in the formulation process, a matrix material (A3) (for example, a clay material) was then added to the mixture of A1 and A2, mixed well to form a homogeneous mixture (A4). This mixture (A4) was then fed to a drier, preferably a spray drier, under conditions sufficient to produce a formulated molecular sieve catalyst composition composed of particles having the desired size and dryness. Spray drying is well known, and is further discussed in this patent specification. The molecular sieve catalyst composition produced is then calcined at an elevated temperature sufficient to further dry and harden the spray dried molecular sieve catalyst composition or formulated molecular sieve catalyst composition. The catalyst composition is then packaged under a dry atmosphere for use, storage or shipment.

Example B
Conversion Process

All catalytic or conversion data presented was obtained using a microflow reactor. The microflow reactor consists of a stainless steel reactor (¼ inch (0.64 cm) outer diameter) located in a furnace to which vaporized methanol is fed. The reactor is maintained at a temperature of 475° C. and a pressure of 25 psig (172.4 kPag). The flow rate of the methanol is such that the flow rate of methanol on weight basis per gram of molecular sieve, also known as the weight hourly space velocity (WHSV) was 100 h$^{-1}$. Product gases exiting the reactor are collected and analyzed using gas chromatography. The molecular sieve alone or the molecular sieve composition load was 50 mg and the reactor bed was diluted with quartz to minimize hot spots in the reactor. In particular, for the catalyst composition of the invention, the molecular sieve and active Group 3 metal oxide or oxide of the Lanthanide or Actinide series elements, a physical mixture of the MSA molecular sieve of Example A and the active metal oxide was used. The total catalyst composition load remained 50 mg, 40 mg of the molecular sieve catalyst composition and 10 mg of the Group 3 metal oxide, and the methanol flow rate was adjusted as the amount of molecular sieve in the reactor bed was changed by the addition of the active metal oxide such that the methanol WHSV was 100 h$^{-1}$ based on the amount of molecular sieve in the reactor bed.

Examples 1 through 7 describe the synthesis of the active metal oxide for use with the molecular sieve catalyst composition, in particularly where the molecular sieve is a SAPO-34. Examples 8 through 15 describe the performance of the molecular sieve catalyst composition and the active metal oxide, with a comparison of the same molecular sieve catalyst composition without an active metal oxide.

Example 1

A sample of La(NO$_3$)$_3$.xH$_2$O (Aldrich Chemical Company) was calcined in air at 700° C. for 3 hours to produce lanthanum oxide.

Example 2

Fifty grams of La(NO$_3$)$_3$.xH$_2$O (Aldrich Chemical Company) were dissolved with stirring in 500 ml of distilled water. The pH was adjusted to 9 by the addition of concentrated ammonium hydroxide. This slurry was then put in polypropylene bottles and placed in a steambox (100° C.) for 72 hours. The product formed was recovered by filtration, washed with excess water, and dried overnight at 85° C. A portion of this catalyst was calcined to 600° C. in flowing air for 3 hours to produce lanthanum oxide (La$_2$O$_3$).

Example 3

Fifty grams of Y(NO$_3$)$_3$.6H$_2$O were dissolved with stirring in 500 ml of distilled water. The pH was adjusted to 9 by the addition of concentrated ammonium hydroxide. This slurry was then put in polypropylene bottles and placed in a steambox (100° C.) for 72 hours. The product formed was recovered by filtration, washed with excess water, and dried overnight at 85° C. A portion of this catalyst was calcined to 600° C. in flowing air for 3 hours to produce yttrium oxide ($Y_2O_3$).

Example 4

A sample of $Sc(NO_3)_3 \cdot xH_2O$ (Aldrich Chemical Company) was calcined in air at 700° C. for 3 hours to produce scandium oxide ($Sc_2O_3$).

Example 5

Fifty grams of $Ce(NO_3)_3 \cdot 6H_2O$ were dissolved with stirring in 500 ml of distilled water. The pH was adjusted to 9 by the addition of concentrated ammonium hydroxide. This slurry was then put in polypropylene bottles and placed in a steambox (100° C.) for 72 hours. The product formed was recovered by filtration, washed with excess water, and dried overnight at 85° C. A portion of this catalyst was calcined to 600° C. in flowing air for 3 hours to produce cerium oxide ($Ce_2O_3$).

Example 6

Fifty grams of $Pr(NO_3)_3 \cdot 6H_2O$ were dissolved with stirring in 500 ml of distilled water. The pH was adjusted to 8 by the addition of concentrated ammonium hydroxide. This slurry was then put in polypropylene bottles and placed in a steambox (100° C.) for 72 hours. The product formed was recovered by filtration, washed with excess water, and dried overnight at 85° C. A portion of this catalyst was calcined to 600° C. in flowing air for 3 hours to produce praseodymium oxide ($Pr_2O_3$).

Example 7

Fifty grams of $Nd(NO_3)_3 \cdot 6H_2O$ were dissolved with stirring in 500 ml of distilled water. The pH was adjusted to 9 by the addition of concentrated ammonium hydroxide. This slurry was then put in polypropylene bottles and placed in a steambox (100° C.) for 72 hours. The product formed was recovered by filtration, washed with excess water, and dried overnight at 85° C. A portion of this catalyst was calcined to 600° C. in flowing air for 3 hours to produce neodymium oxide ($Nd_2O_3$).

Comparative Example 8

In this Comparative Example 8 (CEx. 8) the molecular sieve catalyst composition produced in Example A was tested in accordance with the process of Example B using 50 mg of the molecular sieve catalyst composition without an active metal oxide. The results of the run are presented in Table 1 and Table 2.

Example 9

In this Example 9, the molecular sieve catalyst composition produced in Example A was tested in accordance with the process of Example B using 40 mg of the molecular sieve catalyst composition with 10 mg of $La_2O_3$ produced via nitrate decomposition in Example 1. The components were well mixed and then diluted with sand to form the reactor bed. The results of this Example 9 are shown in Table 1 and Table 2 illustrating that the addition of $La_2O_3$, an active Group 3 metal oxide, increased lifetime by 149%. Selectivity to ethane decreased by 36% and selectivity to propane decreased by 32%, suggesting a significant reduction in hydrogen transfer reactions.

Example 10

In this Example 10, the molecular sieve catalyst composition produced in Example A was tested in accordance with the process of Example B using 40 mg of the molecular sieve catalyst composition with 10 mg of $La_2O_3$ produced via precipitation in Example 2. The components were well mixed and then diluted with sand to form the reactor bed. The results of this Example 10 are shown in Table 1 and Table 2 illustrating that the addition of $La_2O_3$ produced via precipitation, an active Group 3 metal oxide, increased lifetime by 340%. Selectivity to ethane decreased by 55% and selectivity to propane decreased by 44%, suggesting a significant reduction in hydrogen transfer reactions.

Example 11

In this Example 11, the molecular sieve catalyst composition produced in Example A was tested in accordance with the process of Example B using 40 mg of the molecular sieve catalyst composition with 10 mg of $Y_2O_3$ produced in Example 3. The components were well mixed and then diluted with sand to form the reactor bed. The results of this Example 11 are shown in Table 1 and Table 2 illustrating that the addition of $Y_2O_3$, an active Group 3 metal oxide, increased lifetime by 1090%. Selectivity to ethane decreased by 45% and selectivity to propane decreased by 28%, suggesting a significant reduction in hydrogen transfer reactions.

Example 12

In this Example 12, the molecular sieve catalyst composition produced in Example A was tested in accordance with the process of Example B using 40 mg of the molecular sieve catalyst composition with 10 mg of $Sc_2O_3$ produced in Example 4. The components were well mixed and then diluted with sand to form the reactor bed. The results of this Example 12 are shown in Table 1 and Table 2 illustrating that the addition of $Sc_2O_3$, an active Group 3 metal oxide, increased lifetime by 167%. Selectivity to ethane decreased by 27% and selectivity to propane decreased by 21%, suggesting a significant reduction in hydrogen transfer reactions.

Example 13

In this Example 13, the molecular sieve catalyst composition produced in Example A was tested in accordance with the process of Example B using 40 mg of the molecular sieve catalyst composition with 10 mg of $Ce_2O_3$ produced in Example 5. The components were well mixed and then diluted with sand to form the reactor bed. The results of this Example 13 are shown in Table 1 and Table 2 illustrating that the addition of $Ce_2O_3$, an active Lanthanide metal oxide, increased lifetime by 630%. Selectivity to ethane decreased by 50% and selectivity to propane decreased by 34%, suggesting a significant reduction in hydrogen transfer reactions.

Example 14

In this Example 14, the molecular sieve catalyst composition produced in Example A was tested in accordance with the process of Example B using 40 mg of the molecular sieve catalyst composition with 10 mg of $Pr_2O_3$ produced in Example 6. The components were well mixed and then diluted with sand to form the reactor bed. The results of this Example 14 are shown in Table 1 and Table 2 illustrating that the addition of $Pr_2O_3$, an active Lanthanide metal oxide, increased lifetime by 640%. Selectivity to ethane decreased by 51% and selectivity to propane decreased by 38%, suggesting a significant reduction in hydrogen transfer reactions.

Example 15

In this Example 15, the molecular sieve catalyst composition produced in Example A was tested in accordance with the process of Example B using 40 mg of the molecular sieve catalyst composition with 10 mg of $Nd_2O_3$ produced in Example 7. The components were well mixed and then diluted with sand to form the reactor bed. The results of this Example 15 are shown in Table 1 and Table 2 illustrating that the addition of $Nd_2O_3$, an active Lanthanide metal oxide, increased lifetime by 340%. Selectivity to ethane decreased by 49% and selectivity to propane decreased by 34%, suggesting a significant reduction in hydrogen transfer reactions.

TABLE 1

| Example | Reactor Bed Composition | Lifetime Extension Index (LEI) | Prime Olefin (%) | $C_2^=/C_3^=$ | $C_3$ Purity (%) |
|---|---|---|---|---|---|
| CEx. 8 | 100% MSA | 1.0 | 72.99 | 0.90 | 94.1 |
| 9 | 80% MSA/20% $La_2O_3$ | 2.5 | 73.84 | 0.81 | 96.1 |
| 10 | 80% MSA/20% $La_2O_3$ | 4.4 | 73.78 | 0.74 | 96.9 |
| 11 | 80% MSA/20% $Y_2O_3$ | 11.9 | 73.68 | 0.76 | 96.0 |
| 12 | 80% MSA/20% $Sc_2O_3$ | 2.7 | 73.74 | 0.81 | 95.5 |
| 13 | 80% MSA/20% $Ce_2O_3$ | 7.3 | 70.51 | 0.69 | 96.3 |
| 14 | 80% MSA/20% $Pr_2O_3$ | 7.4 | 72.37 | 0.72 | 96.6 |
| 15 | 80% MSA/20% $Nd_2O_3$ | 4.4 | 72.57 | 0.71 | 96.3 |

TABLE 2

| Example | Reactor Bed Composition | $CH_4$ | $C_2^=$ | $C_2^0$ | $C_3^=$ | $C_3^0$ | $C_4$'s | $C_5+$ |
|---|---|---|---|---|---|---|---|---|
| CEx. 8 | 100% MSA | 2.04 | 34.50 | 0.78 | 38.49 | 2.43 | 14.01 | 3.82 |
| 9 | 80% MSA/20% $La_2O_3$ | 1.61 | 33.05 | 0.50 | 40.79 | 1.65 | 14.96 | 4.51 |
| 10 | 80% MSA/20% $La_2O_3$ | 1.38 | 31.43 | 0.35 | 42.35 | 1.37 | 15.03 | 5.51 |
| 11 | 80% MSA/20% $Y_2O_3$ | 1.39 | 31.85 | 0.43 | 41.83 | 1.74 | 14.43 | 5.61 |
| 12 | 80% MSA/20% $Sc_2O_3$ | 1.67 | 33.08 | 0.57 | 40.66 | 1.93 | 14.49 | 4.45 |
| 13 | 80% MSA/20% $Ce_2O_3$ | 2.05 | 28.89 | 0.39 | 41.62 | 1.61 | 15.29 | 6.83 |
| 14 | 80% MSA/20% $Pr_2O_3$ | 1.59 | 30.18 | 0.38 | 42.19 | 1.51 | 15.22 | 6.06 |
| 15 | 80% MSA/20% $Nd_2O_3$ | 1.64 | 30.2 | 0.40 | 42.37 | 1.61 | 15.13 | 5.68 |

While the present invention has been described and illustrated by reference to particular embodiments, those of ordinary skill in the art will appreciate that the invention lends itself to variations not necessarily illustrated herein. For example, it is contemplated that a plug flow, fixed bed or fluidized bed process are used in combination, particularly in different reaction zones within a single or multiple reactor system. It is also contemplated the molecular sieve compositions described herein are useful as absorbents, adsorbents, gas separators, detergents, water purifiers, and for other various uses such as agriculture and horticulture. It is within the scope of this invention to add one or more active Group 3 metal oxide(s) to the synthesis mixture for making a molecular sieve as described above. Also, it is contemplated that one or more molecular sieves are used in the catalyst composition. For this reason, then, reference should be made solely to the appended claims for purposes of determining the true scope of the present invention.

We claim:

1. A process for converting a feedstock comprising contracting one or more oxygenate(s) with one or more olefin(s) in the presence of a molecular sieve catalyst composition comprising a molecular sieve, a binder, a matrix material and a Group 3 metal oxide and/or an oxide of the Lanthanide or Actinide series elements.

2. The process of claim 1 wherein the molecular sieve is synthesized from the combination from at least two of the group consisting of a silicon source, a phosphorous source and an aluminum source, and optionally in the presence of a templating agent.

3. The process of claim 1 wherein the metal of the Group 3 metal oxide or the oxide of the Lanthanide or Actinide series elements is selected from one of the group consisting of scandium, yttrium, lanthanum, cerium, praseodymium and neodymium.

4. The process of claim 1 wherein the metal of Group 3 metal oxide is yttrium.

5. The process of claim 1 wherein the Group 3 metal oxide or the oxide of the Lanthanide or Actinide series element is selected from one of the group consisting of lanthanum oxide, yttrium oxide, scandium oxide, cerium oxide, praseodymium oxide and neodymium oxide, or mixtures thereof.

6. The process of claim 1 wherein the molecular sieve catalyst composition has a Lifetime Enhancement Index (LEI) greater than 1.1.

7. The process of claim 1 wherein the molecular sieve is a silicoaluminophosphate molecular sieve and/or an aluminophosphate molecular sieve.

8. The process of claim 1 wherein the oxygenate(s) comprises methanol and/or dimethylether.

9. The process of claim 1 wherein the olefins(s) include ethylene and propylene, the molecular sieve is a silicoaluminophosphate molecular sieve, the oxygenate(s) comprises methanol, the Group 3 metal oxide is yttrium oxide, the binder is an alumina sol, and the matrix material is a clay.

10. A process for producing one or more olefin(s), the process comprising the steps of:

(a) introducing a feedstock comprising at least one oxygenate to a reactor system in the presence of a molecular sieve catalyst composition comprising a molecular sieve, a binder, a matrix material, and a Group 3 metal oxide and/or an oxide of the Lanthanide or Actinide series elements;

(b) withdrawing from the reactor system an effluent stream; and (c) passing the effluent stream through a recovery system; and (d) recovering at least the one or more olefin(s).

11. The process of claim 10 wherein the binder is an alumina sol.

12. The process of claim 10 wherein the matrix material is a clay.

13. The process of claim 10 wherein the molecular sieve is a silicoaluminophosphate molecular sieve and/or an aluminophosphate molecular sieve.

14. The process of claim 10 wherein the Group 3 metal oxide is a lanthanum oxide or a yttrium oxide or a mixture thereof.

15. The process of claim 10 wherein the feedstock comprises methanol and/or dimethylether.

16. The process of claim 10 wherein the LEI of the molecular sieve catalyst composition is greater than that for the same molecular sieve catalyst composition without the Group 3 metal oxide or the oxide of the Lanthanide or Actinide series elements.

17. The process of claim 10 wherein the Group 3 metal oxide is yttrium oxide.

18. The process of claim 10 wherein the molecular sieve catalyst composition has a LEI greater than 1.5.

19. The process of claim 10 wherein the olefin(s) include ethylene and propylene.

20. A process for converting a feedstock comprising contracting one or more oxygenate(s) with one or more olefin(s) in the presence of a molecular sieve catalyst composition prepared by a method for making the molecular sieve catalyst composition, the method comprising the steps of: (i) forming an active Group 3 metal oxide or an active oxide of a Lanthanide or Actinide series element, (ii) synthesizing a molecular sieve from the combination of at least two of the group consisting of a silicon source, a phosphorous source and an aluminum source, optionally in the presence of a templating agent, and (iii) introducing a binder, optionally with a matrix material.

21. A process for converting a feedstock comprising contracting one or more oxygenate(s) with one or more olefin(s) in the presence of a molecular sieve composition prepared by a method of making the molecular sieve composition, the method comprising the steps of: (i) synthesizing a molecular sieve by the method comprising the steps of: (a) forming a first reaction mixture of at least one templating agent and at least two of the group consisting of a silicon source, a phosphorous source and an aluminum source; and (b) removing the molecular sieve from the first reaction mixture; (ii) forming an active metal oxide by the method comprising the steps of: (a) forming a second reaction mixture comprising a Group 3 or Lanthanide or Actinide series element metal oxide precursor and a precipitating agent, (b) removing the active metal oxide from the second reaction mixture; and (iii) combining the molecular sieve and the active metal oxide.

22. An integrated process for making one or more olefin(s), the integrated process comprising the steps of:

(a) passing a hydrocarbon feedstock to a syngas production zone to produce a synthesis gas stream;

(b) contacting the synthesis gas stream with a catalyst to form an oxygenated feedstock; and (c) converting thin oxygenated feedstock into the one or more olefin(s) in the presence of a molecular sieve catalyst composition comprising a molecular sieve and an active metal oxide, the metal selected from Group 3 or Lanthanide or Actinide series elements of the Periodic Table of Elements.

23. The integrated process of claim 22 wherein the oxygenated feedstock comprises methanol and the olefin(s) include ethylene and propylene.

24. The integrated process of claim 22 wherein the molecular sieve is a silicoaluminophosphate molecular sieve.

* * * * *